(12) United States Patent
Beller et al.

(10) Patent No.: US 6,235,910 B1
(45) Date of Patent: May 22, 2001

(54) PROCESS FOR THE PREPARATION OF IMIDAZOLIDINE-2, 4-DIONES

(75) Inventors: Matthias Beller, Rostock; Markus Eckert, Köln; Wahed Moradi, Rostock, all of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/400,311

(22) Filed: Sep. 21, 1999

(30) Foreign Application Priority Data

Sep. 22, 1998 (DE) .............................. 198 43 299

(51) Int. Cl.⁷ ................................................. C07D 233/40
(52) U.S. Cl. ............................................................ 548/317.1
(58) Field of Search ........................................... 548/317.1

(56) References Cited

FOREIGN PATENT DOCUMENTS

| 196 29 717 C1 | 2/1998 | (DE) . |
|---|---|---|
| 0 091 596 A2 | 10/1983 | (EP) . |
| 2 012 756 | 8/1979 | (GB) . |

OTHER PUBLICATIONS

Beller, Matthias et al., "A new class of catalysts with superior activity and selectivity for amidocarbonylation reactions," Journal of Molecular Catalysis A: Chemical 135 (1998) 23–33.
Beller et al., "A New Class of Catalysts With Superior Activity and Selectivity for *Amidocarbonylation* Reactions", Abstract, C.A. 130, Nr. 25272 (1998).

Primary Examiner—Floyd D. Higel
Assistant Examiner—Ebenezer Sackey
(74) Attorney, Agent, or Firm—Pillsbury Winthrop LLP

(57) ABSTRACT

A process for the preparation of compounds of the general formula (I)

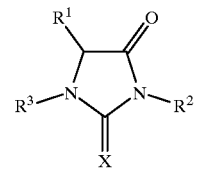

I by reacting an aldehyde compound of the general formula (II)

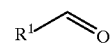

II with a urea compound of the general formula (III)

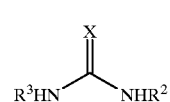

III in the presence of carbon monoxide and a catalytically active metal compound. Compounds of the general formula (I) are important intermediates for the synthesis of α-amino acids.

19 Claims, No Drawings

PROCESS FOR THE PREPARATION OF IMIDAZOLIDINE-2, 4-DIONES

CROSS-REFERENCE TO RELATED APPLICATION

This application is based on German Application DE 198 43 299.2, filed Sep. 22, 1998, which disclosure is incorporated herein by reference.

FIELD OF THE INVENTION

The present invention relates to a process for the preparation of compounds of the general formula (I)

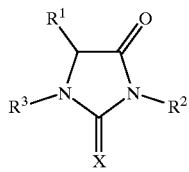

wherein
X denotes oxygen, sulfur or selenium and
$R^1$ denotes H, $(C_1-C_{18})$-alkyl, $(C_2-C_{18})$-alkenyl, $(C_2-C_{18})$-alkinyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, where the above-mentioned radicals can be mono- or polysubstituted by heteroatoms, such as Hal, $NR^1R^2$, $PO_{0-3}R^1R^2$, $OPO_{0-3}R^1R^2$, $OR^1$, $SR^1$, $SOR^1$, $SO_2R^1$, $SO_3R^1$, or groups such as $CO_2H$, $CO_2R^1$, $CONH_2$, $CONHR^1$ or one or more $CH_2$ groups can be substituted by heteroatoms, such as $NR^1$, $PR^1$, O or S,
$R_2$ denotes H, $(C_1-C_{18})$-alkyl, $(C_2-C_{18})$-alkenyl, $(C_2-C_{18})$-alkinyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, where the above-mentioned radicals can be mono- or polysubstituted by heteroatoms, such as Hal, $NR^1R^2$, $PO_{0-3}R^1R^2$, $OPO_{0-3}R^1R^2$, $OR^1$, $SR^1$, $SOR^1$, $SO_3R^1$ or one or more $CH_2$ groups can be substituted by heteroatoms, such as $NR^1$, $PR^1$, O or S,
$R_3$ denotes H, $(C_1-C_{18})$-alkyl, $(C_2-C_{18})$-alkenyl, $(C_2-C_{18})$-alkinyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, where the above-mentioned radicals can be mono- or polysubstituted by heteroatoms, such as Hal, $NR^1R^2$, $PO_{0-3}R^1R^2$, $OPO_{0-3}R^1R^2$, $OR^1$, $SR^1$, $SOR^1$, $SO_3R^1$ or one or more $CH_2$ groups can be substituted by heteroatoms, such as $NR^1$, $PR^1$, O or S. The invention furthermore relates to a use of the compounds of the general formula (I).

BACKGROUND OF THE INVENTION

Compounds of the general formula (I) are important starting substances for the synthesis of racemic and enantiomerically enriched α-amino acids, which in turn are required for the synthesis of bioactive substances or for the nutritional requirements of animals and humans.

Imidazolidine-2,4-diones which are unsubstituted in the 1- and 3-position can be obtained from the reaction of an aldehyde (RCHO), hydrocyanic acid (HCN) and ammonium carbonate via the so-called Bucherer-Bergs reaction. Although this reaction is used industrially, it has the disadvantage that extremely toxic hydrocyanic acid must be employed as a starting material, and that imidazolidine-2, 4-diones which are substituted in the 3-position are not directly accessible.

Imidazolidine-2,4-diones which also carry a substituent in the 3-position in addition to the 5-position are therefore advantageously prepared from the corresponding amino acid and an isocyanate. This process has the disadvantage that comparatively expensive amino acids must be employed as educts, and that only a few isocyanates are commercially available on an industrial scale.

1,3,5-Substituted hydantoins can be prepared from the corresponding, very expensive, N-substituted amino acid and an isocyanate (Advances in Heterocyclic Chemistry, vol. 38, 1985, 177–228). This process also has the disadvantages described above. In the case of amino acids which are not naturally occurring (not proteinogenic), the corresponding amino acid must additionally be prepared beforehand in several stages. There is, therefore, to date no practicable one-stage process which allows the preparation of 1,3,5-substituted hydantoins from inexpensive starting compounds.

SUMMARY OF THE INVENTION

The object of the present invention, therefore, is to provide a process for the preparation of compounds of the general formula (I) which does not involve the above-mentioned prior art disadvantages, and which in particular, allows the synthesis of compounds of the general formula (I) in fewer reaction steps, starting from inexpensive educts, which present fewer health risks and produce good yields on an industrial scale.

DETAILED DESCRIPTION OF THE INVENTION

Compounds of the general formula (I)

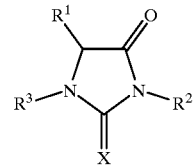

wherein
X denotes oxygen, sulfur or selenium and
$R^1$ denotes H, $(C_1-C_{18})$-alkyl, $(C_2-C_{18})$-alkenyl, $(C_2-C_{18})$-alkinyl, $(C_6-C_{18})$-aryl $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, where the above-mentioned radicals can be mono- or polysubstituted by heteroatoms, such as Hal, $NR^1R^2$, $PO_{0-3}R^1R^2$, $OPO_{0-3}R^1R^2$, $OR^1$, $SR^1$, $SOR^1$, $SO_2R^1$, $SO_3R^1$, or groups such as $CO_2H$, $CO_2R^1$, $CONH_2$, $CONHR^1$ or one or more $CH_2$ groups can be substituted by heteroatoms, such as $NR^1$, $PR^1$, O or S, $R^2$ denotes H, $(C_1-C_{18})$-alkyl, $(C_2-C_{18})$-alkenyl, $(C_2-C_{18})$-alkinyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, where the above-mentioned radicals can be mono- or polysubstituted by heteroatoms, such as Hal, $NR^1R^2$, $PO_{0-3}R^1R^2$, $OPO_{0-3}R^1R^2$, $OR^1$, $SR^1$, $SOR^1$, $SO_2R^1$, $SO_3R^1$, or groups such as $CO_2H$, $CO_2R^1$, $CONH_2$, $CONHR^1$ or one or more $CH_2$ groups can be substituted by heteroatoms, such as $NR^1$, $PR^1$, O or S, $R^3$ denotes H, $(C_1-C_{18})$-alkyl, $(C_2-C_{18})$-alkenyl, $(C_2-C_{18})$-alkinyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroalkyl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, where the above-mentioned radicals can be mono- or polysubstituted by heteroatoms, such as Hal, $NR^1R^2$, $PO_{0-3}R^1R^2$, $OPO_{0-3}R^1R^2$, $OR^1$, $SR^1$, $SOR^1$, $SO_2R^1$, $SO_3R^1$, or groups such as $CO_2H$, $CO_2R^1$, $CONH_2$, $CONHR^1$ or one or more $CH_2$ groups can be substituted by heteroatoms, such as $NR^1$, $PR^1$, O or S, are produced by reaction of an aldehyde compound of the general formula (II)

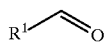

II wherein $R^1$ is defined above, with a urea compound of the general formula (III)

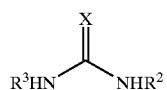

III wherein X, $R^2$ and $R^3$ are defined above, in the presence of carbon monoxide (CO) and a catalytically active metal compound. The desired derivatives are obtained with good to very good yields, starting from inexpensive educts in a one-stage process which is easy to carry out industrially, and avoids the use of extremely toxic hydrocyanic acid.

Compounds of the general formula (I) wherein X represents oxygen, $R^1$ denotes a radical chosen from the group consisting of methyl, ethyl, isopropyl, n-butyl, sec-butyl, isobutyl, tert-butyl, methylthioethyl, thiomethyl, methoxycarbonylmethyl, methoxycarbonylethyl, phenyl, 2-, 3-, 4-pyridyl, benzyl, 1-, 2-phenylethyl, hydroxymethyl, hydroxyethyl, vinyl, methoxymethyl, methoxyethyl, carboxymethyl, carboxyethyl, acetamidomethyl, acetamidoethyl, chloromethyl, chloroethyl, methylphosphonoethyl, 2-ethylhexyl, tetradecyl, hexadecyl and $R^2$ and $R^3$ independently of one another can denote hydrogen, methyl, ethyl, butyl, phenyl, benzyl, 2-ethylhexyl, are preferred.

Any desired aldehyde $R^1CHO$, wherein $R^1$ has the above-mentioned definition, can be used according to the invention as educts. Examples of suitable aldehydes $R^1CHO$ are formaldehyde, acetaldehyde, propionaldehyde, butyraldehyde, valeraldehyde, 2-ethylhexanal, 2-ethylhexenal, isobutyraldehyde, furfural, crotonaldehyde, acrolein, benzaldehyde, substituted benzaldehydes, phenylacetaldehyde, 2,4-dihydroxyphenylacetaldehyde, glyoxalic acid, methoxyacetaldehyde, chloroacetaldehyde, 3-thiopropionaldehyde and α-acetoxypropionaldehyde. Dialdehyde compounds and trialdehyde compounds can also be employed. Substances which can form an aldehyde under the reaction conditions mentioned above, e.g., aldehyde oligomers, such as paraformaldehyde; acetals, such as acetaldehyde dimethyl acetal; allyl alcohols; and epoxides, such as phenyloxirane, are also suitable starting materials.

Any desired urea compound can be employed in the process according to the invention. Examples of suitable urea compounds are urea, thiourea, selenourea, N-methylurea, N,N'-dimethylurea, N-methylthiourea, N,N'-dimethylthiourea, N-benzylurea, N-phenylurea, N,N'-diphenylurea, N-phenylthiourea, N-ethylurea, N-methyl-, N'-phenylurea. If urea and/or monosubstituted ureas are used, the non-cyclized carbamoylamino acids can also be formed in addition to the desired hydantoins. However, these by-products can be cyclized by a longer reaction time or addition of a dehydrating agent, so that only the desired hydantoins are formed. If the synthesis of carbamoylamino acids or carbamoylamino acid esters is desired, these can be prepared by hydrolysis of the hydantoins in the presence of water, alcohols or hydrolyzing enzymes.

The reaction can advantageously be carried out in the presence of an acid with a pKa value of <5. All organic or inorganic acids available to the expert for this purpose may be used as the acid, such as, for example, HCl, HBr, sulfuric acid, phosphoric acid, trifluoroacetic acid, trifluoromethylsulfonic acid, p-toluenesulfonic acid, methanesulfonic acid, formic acid, oxalic acid, HI, benzoic acid, acetic acid or a mixture thereof.

The use of sulfuric acid or a hydrogen halide, such as HCl, HI or HBr, for this purpose is particularly preferred.

Possible catalytically active metal compounds are all catalysts with which the expert is familiar for this purpose. These are preferably compounds of metals of sub-group 7 or 8 of the periodic table of elements.

Metal catalysts from palladium compounds or cobalt compounds are particularly preferred.

Cobalt carbonyls, e.g. solid $Co_2(CO)_8$, are preferably employed as cobalt catalysts or precatalysts. However, the cobalt carbonyl can also be formed in situ from known cobalt(II) and cobalt(III) compounds, such as e.g. cobalt(II) acetate, cobalt(II) chloride, cobalt(II) bromide, in the presence of CO, optionally with addition of $H_2$.

Palladium catalysts or precatalysts which can be employed are any desired palladium(II) compounds, palladium(0) compounds and palladium on support materials, such as, for example, palladium-on-active charcoal. Examples of palladium(II) compounds are palladium acetate, palladium halides, palladium nitrites, palladium nitrates, palladium carbonates, palladium ketonates, palladium acetylacetonates and allyl-palladium complexes. Particularly preferred representatives are $PdBr_2$, $PdCl_2$, $Li_2PdBr_4$, $Li_2PdCl_4$ and $Pd(OAc)_2$. Examples of palladium (0) compounds are palladium-phosphine complexes and palladium-olefin complexes. Particularly preferred representatives are palladium-(dba) complexes (dba=dibenzylideneacetone) and $Pd(PPh_3)_4$.

If palladium-phosphine complexes are employed, bisphosphine-palladium(II) compounds have moreover proved to be particularly suitable. The complexes can be employed as such or produced in the reaction mixture from a palladium-II compound, such as e.g. $PdBr_2$, $PdCl_2$ or palladium-II acetate, with the addition of phosphines, such as e.g. triphenylphosphine, tritolylphosphine, bis- (diphenylphosphino)-ethane, 1,4-bis-(diphenylphosphino)-butane or 1,3-bis-(diphenylphosphino)-propane.

Of the palladium-phosphine complexes mentioned, bis-triphenylphosphine-palladium(II) bromide-$PdBr_2(PPh_3)^{2-}$ and the corresponding chloride are particularly preferred. These complexes can be employed as such or produced in the reaction mixture from palladium(II) bromide or chloride and triphenylphosphine.

The use of $Ir^{+1}$ compounds, such as $[Ir(COD)Cl]_2$, $[Ir(COD)_2]^+BF_4^-$, $Ph_3PIrCl(CO)$, $Ir(CO)_2acac$, $Ph_3PIrH(CO)$, and $Ir^{+3}$ compounds, such as $IrCl_3$, $IrBr_3$, $Ir(acac)_3$, $Ir_4(CO)_{12}$ or $Ir(OAc)_3$, is furthermore particularly preferred. In addition, Mn catalysts in oxidation levels 0, +2, +3 and +4, such as $Mn_2(CO)_{10}$, $MnBr_2$ and $Mn(OAc)_3$, are also suitable as catalysts or precatalysts for the process according to the invention.

For the present process, it has been found that an amount of 0.0001 to 5 mol % of the catalytically active metal compound (calculated for the metal), preferably of 0.001–4 mol %, and particularly preferably of 0.01–2 mol %, based on the urea of formula (III), is sufficient.

A halide salt can preferably be added to the reaction as a cocatalyst. Halide salts which can be used are e.g. phosphonium bromides and phosphonium iodides, e.g. tetrabutylphosphonium bromide or tetrabutylphosphonium iodide, and ammonium, lithium, sodium, potassium chloride, bromide and iodide. Preferred halides are the chlorides and bromides. The ionic halide is preferably employed in an amount of 1 to 100 mol %, in particular 2–40 mol %, and especially preferably 5–30 mol %, based on the urea of formula (III).

Water and all organic solvents familiar to the expert for carrying out this type of reaction, can be employed as a solvent. Dipolar aprotic compounds can preferably be employed. Examples of these are dioxane, tetrahydrofuran, N-methylpyrrolidone, ethylene glycol dimethyl ether, ethyl acetate, acetic acid, acetonitrile, benzonitrile, tert-butyl methyl ether, dibutyl ether, sulfolane, DMSO, N,N-dimethylacetamide. or mixtures thereof. The solvents can be employed in the pure form or in a form containing product or saturated with product. N-methylpyrrolidone, dimethylformamide and acetonitrile are particularly preferred as the solvent.

The reaction can be carried out under pressures of 1 to 250 bar, preferably 10 to 150 bar.

The process according to the invention is relatively non-critical with respect to temperature. The reaction can be carried out at temperatures of 0–200° C., preferably 50–150° C.

The aldehyde of formula (II) is expediently employed in an amount of 0.5 to 5 equivalents, preferably 0.8 to 2 equivalents, based on the urea of formula (III).

By using chiral enantiomerically enriched ligands in combination with the catalytically active metal compound, enantiomerically enriched hydantoins or, after hydrolysis, enantiomerically enriched α-amino acids can also be obtained by means of this process. Possible chiral ligands are all ligands known to the expert which coordinate on the catalytically active metal compound. An overview of the possible ligands is given in I. Ojima, Catalytic Asymmetric Synthesis, VCH, New York, 1993, which is hereby incorporated by reference.

Ligands such as 1-diphenylphosphino-1-phenylethane, 1-diphenylphosphino-1-naphthylethane, DIOP, BINAP, MOP, 1-diphenylphosphino-1-ferro-cenylethane, 3,4-carbophos, duphos, BPPM, BPE, DIPAMP, propraphos, deguphos, chiraphos, norphos, bichep, MCCPM, josiphos, bimop are particularly preferred here.

In another aspect of the invention, compounds of the general formula (I) can be used for the synthesis of α-amino acids. The enzymatic or chemical hydrolysis of the hydantoins (I) to give the α-amino acids is described e.g. in Enzyme Catalysis in Organic Synthesis, K. Drauz, H. Waldmann (eds.), VCH-Wiley, 1995 or Houben-Weyl, vol. 11/2, Thieme Verlag, 1958, p. 368 et seq, herein incorporated by reference.

Aldehydes readily react with ureas in an acid medium to give undesirable 2-oxo-1,2,3,4-tetrahydropyrimidines (Monatshefte Chem. 1965, 96, 1950–1966). It is, therefore, surprising that the hydantoins of the general formula (I) can be obtained with high selectivity in a one-pot process as described above. Furthermore, it would have been expected that hydantoins are opened by the water formed during the condensation reaction, to give the corresponding N-carbamoylamino acid, which, however, does not occur to the expected extent.

A $(C_1-C_{18})$-alkyl radical in the context of the invention is understood to mean a radical having 1 to 18 saturated C atoms, which can have any desired branchings. The radicals methyl, ethyl, n-propyl, isopropyl, n-butyl, isobutyl, sec-butyl, tert-butyl, pentyl, hexyl etc. can be subsumed, in particular, under this group. A $(C_1-C_8)$-alkyl radical describes the radical just defined in an extent of 1 to 8 C atoms.

A $(C_2-C_{18})$-alkenyl radical has the features mentioned for the $(C_1-C_{18})$-alkyl radical, where at least one double bond must be present within the radical.

A $(C_2-C_{18})$-alkinyl radical has the features mentioned for the $(C_1-C_{18})$-alkyl radical, where at least one triple bond must be present within the radical.

A $(C_6-C_{18})$-aryl radical is understood to mean an aromatic radical having 6 to 18 C atoms. This includes, in particular, residues such as phenyl, naphthyl, anthryl, phenanthryl, biphenyl radicals.

A $(C_7-C_{19})$-aralkyl radical is a $(C_6-C_{18})$-aryl radical bonded to the molecule via a $(C_1-C_8)$-alkyl radical.

In the context of the invention, a $(C_3-C_{18})$-heteroaryl radical designates a five-, six- or seven-membered aromatic ring system of 3 to 18 C atoms which contains heteroatoms such as e.g., nitrogen, oxygen or sulfur in the ring. Radicals such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl, in particular, are considered to be such heteroaromatics.

A $(C_4-C_{19})$-heteroaralkyl is understood to mean a heteroaromatic system corresponding to the $(C_7-C_{19})$-aralkyl radical.

In the context of the invention, a $(C_3-C_8)$-cycloalkyl radical consequently designates a radical of the group of cyclic alkyl radicals having 3 to 8 C atoms and optionally any desired branching. The radicals cyclopropyl, cyclobutyl, cyclopentyl, cyclohexyl, cycloheptyl in particular are to be subsumed under this group. One or more double bonds can be present in this radical.

The alkyl, alkenyl and aryvheteroaryl groups mentioned above, can additionally be substituted by $NO_2$, NO, NOH, $NNH_2$, $NN[(C_1-C_8)\text{-alkyl}]_2$, $NNH\text{-}(C_1-C_8)\text{-alkyl}$, CN, CHO, $NHCO\text{-}(C_1-C_{18})\text{-alkyl}$, $CO\text{-}(C_1-C_{18})\text{-alkyl}$, NHCHO, $CO\text{-}(C_1-C_{18})\text{-aryl}$, $CO_2\text{-}(C_1-C_{18})\text{-aryl}$, $CF_3$, $CCl_3$, $CON[(C_1-C_{18})\text{-alkyl}]_2$, $OCO\text{-}(C_1-C_{18})\text{-alkyl}$, $OCONH\text{-}(C_1-C_{18})\text{-alkyl}$, $OCON[(C_1-C_{18})\text{-alkyl}]_2$, $CONH\text{-}(C_6-C_{18})\text{-aryl}$, $CON[(C_6-C_{18})\text{-aryl}]_2$, $OCO\text{-}(C_6-C_{18})\text{-aryl}$, $OCONH\text{-}(C_6-C_{18})\text{-aryl}$, $OCON[(C_6-C_{18})\text{-aryl}]_2$, $CHCHCO_2\text{-}(C_1-C_{12})\text{-alkyl}$, $Si[(C_1-C_{18})\text{-alkyl}]_3$, $Si[O\text{-}(C_1-C_{18})\text{-alkyl}]_3$, or $Si[NH\text{-}(C_1-C_{18})\text{-alkyl}]_3$.

Hal is understood to mean fluorine, chlorine, bromine, iodine.

In the context of the invention, the term enantiomerically enriched is understood to mean the content of one enantiomer in a mixture with its optical antipode has a range of >50% and <100%.

The substituent $-PO_{0-3}R^1R^2$ is understood to mean all radicals corresponding to this empirical formula, regardless of whether the radicals $R^1$ and $R^2$ are bonded to the phosphorus atom directly or via an oxygen. The following examples are intended to illustrate the process.

EXAMPLE 1

2,800 g cyclohexanecarbaldehyde, 1,500 g urea, 25 ml N-methylpyrrolidone, 0.017 g palladium(II) bromide, 0.033 g triphenylphosphane, 0.100 g sulfuric acid and 0.760 g lithium bromide are reacted in a 300 ml autoclave under 60 bar at 100C. After a reaction time of 12 hours, the solvent is removed in vacuo and the residue is analyzed by means of high pressure liquid chromatography (HPLC). 3,200 g 5-cyclohexyl-hydantoin are formed. This corresponds to a yield of 70%.

EXAMPLE 2

2,800 g cyclohexanecarbaldehyde, 1,900 g N-methylurea, 25 ml N-methylpyrrolidone, 0.017 g palladium(II) bromide, 0.033 g triphenylphosphane, 0.100 g sulfuric acid and 0.760 g lithium bromide are reacted in a 300 ml autoclave under 60 bar at 80° C. After a reaction time of 12 hours, the solvent is removed in vacuo and the residue is analyzed by means of high pressure liquid chromatography (HPLC). 4,200 g 5-cyclohexyl-3-methylhydantoin are formed. This corresponds to a yield of 86%.

EXAMPLE 3

2,600 g benzaldehyde, 1,500 g urea, 25 ml N-methylpyrrolidone, 0.017 g palladium(II) bromide, 0.033 g triphenylphosphane, 0.100 9 sulfuric acid and 0.760 g lithium bromide are reacted in a 300 ml autoclave under 60 bar at 80° C. After a reaction time of 12 hours, the solvent is removed in vacuo and the residue is analyzed by means of high pressure liquid chromatography (HPLC). 2,200 g 5-phenylhydantoin are formed. This corresponds to a yield of 50%.

EXAMPLE 4–10

The following hydantoins were prepared analogously to example 1 (table 1):

| Example (X = 0) | Temperature (° C.) | $R^3$ | $R^2$ | $R^1$ | Yield (%) |
|---|---|---|---|---|---|
| 4 | 80 | H | Me | Ph | 75 |
| 5 | 100 | Me | Me | Cyclohexyl | 79 |
| 6 | 100 | Me | Me | Ph | 85 |
| 7 | 120 | Me | Me | Isobutyl | 55 |
| 8 | 100 | H | Ph | Cyclohexyl | 64 |
| 9 | 100 | H | Bz | Ph | 50 |
| 10 | 100 | H | Et | Cyclohexyl | 51 |

EXAMPLE 11

Active Charcoal

The reaction was carried out analogously to Example 1, but 1 mol % Pd-on-active charcoal was used as the catalyst. 4,300 g 5-cyclohexyl-3-methylhydantoin were obtained. This corresponds to a yield of 88%.

What is claimed is:

1. A process for the preparation of compounds of the formula (I)

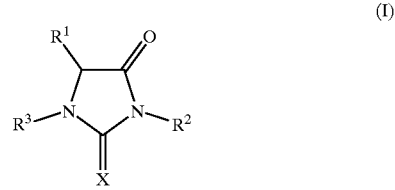

wherein

X denotes oxygen, sulfur or selenium and $R^1$ denotes —H, $(C_1$–$C_{18})$-alkyl, $(C_2$–$C_{18})$-alkenyl, $(C_2$–$C_{18})$-alkinyl, $(C_6$–$C_{18})$-aryl, $(C_7$–$C_{19})$-aralkyl, $(C_3$–$C_{18})$-heteroaryl, $(C_4$–$C_{19})$-heteroaralkyl, $(C_1$–$C_8)$-alkyl-$(C_6$–$C_{18})$-aryl, $(C_1$–$C_8)$-alkyl-$(C_3$–$C_{19})$-heteroalkyl, $(C_3$–$C_8)$-cycloalkyl, $(C_1$–$C_8)$-alkyl-$(C_3$–$C_8)$-cycloalkyl, $(C_3$–$C_8)$-cycloalkyl- or $(C_1$–$C_8)$-alkyl radicals, $R^2$ denotes —H, $(C_1$–$C_{18})$-alkyl, $(C_2$–$C_{18})$-alkenyl, $(C_2$–$C_{18})$-alkinyl, $(C_6$–$C_{18})$-aryl, $(C_7$–$C_{19})$-aralkyl, $(C_3$–$C_{18})$-heteroaryl, $(C_4$–$C_{19})$-heteroaralkyl, $(C_1$–$C_8)$-alkyl-$(C_6$–$C_{18})$-aryl, $(C_1$–$C_8)$-alkyl-$(C_3$–$C_{19})$-heteroalkyl, $(C_3$–$C_8)$-cycloalkyl, $(C_1$–$C_8)$-alkyl-$(C_3$–$C_8)$-cycloalkyl, $(C_3$–$C_8)$-cycloalkyl- or $(C_1$–$C_8)$-alkyl radicals, $R^3$ denotes —H, $(C_1$–$C_{18})$-alkyl, $(C_2$–$C_{18})$-alkenyl, $(C_2$–$C_{18})$-alkinyl, $(C_6$–$C_{18})$-aryl, $(C_7$–$C_{19})$-aralkyl, $(C_3$–$C_{18})$-heteroaryl, $(C_4$–$C_{19})$-heteroaralkyl, $(C_1$–$C_8)$-alkyl-$(C_6$–$C_{18})$-aryl, $(C_1$–$C_8)$-alkyl-$(C_3$–$C_{19})$-heteroalkyl, $(C_3$–$C_8)$-cycloalkyl, $(C_1$–$C_8)$-alkyl-$(C_3$–$C_8)$-cycloalkyl, $(C_3$–$C_8)$-cycloalkyl- or $(C_1$–$C_8)$-alkyl radicals, comprising reacting an aldehyde compound of the general formula (II)

wherein $R^1$ is defined above, with a urea compound of the general formula (III)

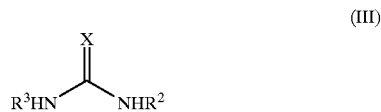

wherein X, $R^2$ and $R^3$ are defined above, in the presence of carbon monoxide (CO) and a catalytically active metal compound.

2. The process according to claim 1, wherein

X denotes oxygen, $R^1$ denotes a radical chosen from the group consisting of methyl, ethyl, isopropyl, n-butyl, sec-butyl, isobutyl, tert-butyl, methylthioethyl, thiomethyl, methoxycarbonylmethyl, methoxycarbonylethyl, phenyl, 2-, 3-, 4-pyridyl, benzyl, 1-, 2-phenylethyl, hydroxymethyl, hydroxyethyl, vinyl, methoxymethyl, methoxyethyl, carboxymethyl, carboxyethyl, acetamidomethyl, acetamidoethyl, chloromethyl, chloroethyl, methylphosphonoethyl, 2-ethylhexyl, tetradecyl and hexadecyl, and $R^2$ and $R^3$ independently of one another can denote hydrogen, methyl, ethyl, butyl, phenyl, benzyl, 2-ethylhexyl.

3. The process according to claim 1, wherein the reaction is carried out in the presence of an acid with a pKa value of <5.

4. The process according to claim 1, wherein the reaction is carried out in the presence of sulfuric acid or a hydrogen halide.

5. The process according to claim 1, wherein a compound of Pd, Co, $Ir^{+1}$, $Ir^{+3}$, Mn, $Mn^{+2}$ or $Mn^{+3}$ is present as the catalytically active metal compound during the reaction.

6. The process according to claim 1, wherein the catalyst is employed in an amount of 0.0001 to 5 mol %, based on the urea of formula (III).

7. The process according to claim 6, wherein the catalyst is employed in an amount of 0.01 to 2 mol %, based on the urea compound of formula (III).

8. The process according to claim 1, wherein a halide salt is added to the reaction in a concentration of 0.1 to 100 mol %, based on the urea compound of formula (III).

9. The process according to claim 1, wherein N-methylpyrrolidone, dimethylformamide or acetonitrile is employed as a solvent.

10. The process according to claim 1, wherein the reaction is carried out under a CO pressure of 1–250 bar.

11. The process according to claim 10, wherein the reaction is carried out under a CO pressure of 10–150 bar.

12. The process according to claim 1, wherein the reaction is carried out at a temperature of 0 to 200° C.

13. The process according to claim 1, wherein the reaction is carried out at a temperature of 50 to 150° C.

14. The process according to claim 1, wherein the aldehyde of formula (I) is employed in the reaction in an amount of 0.5 to 5 equivalents.

15. The process according to claim 5, wherein the catalytically active metal compound is chirally modified.

16. The process according to claim 1, wherein the compound of formula (I) is further hydrolyzed to form an α-amino acid.

17. The process according to claim 1, wherein the $R^1$ radicals are mono- or polysubstituted by Hal, $—NR^1R^2$, $—PO_{0-3}R^1R^2$, $—OPO_{0-3}R^1R^2$, $—OR^1$, $—SR^1$, $—SOR^1$, $—SO_2R^1$, $—SO_3R^1$, $—CO_2H$, $—CO_2R^1$, $—CONH_2$, $—CONHR^1$, or one or more $—CH_2—$ groups substituted by $—NR^1$, $—PR^1$, $—O—$ or $—S—$.

18. The process according to claim 1, wherein the $R^2$ radicals are mono- or polysubstituted by Hal, $—NR^1R^2$, $—PO_{0-3}R^1R^2$, $—OPO_{0-3}R^1R^2$, $—OR^1$, $—SR^1$, $—SOR^1$, $—SO_2R^1$, $—SO_3R^1$, or one or more $—CH_2—$ groups substituted by $—NR^1$, $—PR^1$, $—O—$ or $—S—$.

19. The process according to claim 1, wherein the $R^3$ radicals are mono- or polysubstituted by Hal, $—NR^1R^2$, $—PO_{0-3}R^1R^2$, $—OPO_{0-3}R^1R^2$, $—OR^1$, $—SR^1$, $—SOR^1$, $—SO_2R^1$, $—SO_3R^1$, or one or more $—CH_2—$ groups substituted by $—NR^1$, $—PR^1$, $—O—$ or $—S—$.

* * * * *